United States Patent [19]

Kisfaludy et al.

[11] 4,179,433

[45] Dec. 18, 1979

[54] ANGIOTENSIN II ANTAGONIST PEPTIDES CONTAINING AN ALPHA-AMINOOXYACID IN THE POSITION-1

[75] Inventors: Lajos Kisfaludy; Olga Nýeki née Kuprina; Maria Skirmai née Sárközi; Egon Kárpáti; Katalin Gidai; László Szporny, all of Budapest, Hungary

[73] Assignee: Richter Gedeon Vegyeszeti Gyar Rt., Budapest, Hungary

[21] Appl. No.: 923,681

[22] Filed: Jul. 11, 1978

[30] Foreign Application Priority Data

Jul. 18, 1977 [HU] Hungary .................................. RI 640

[51] Int. Cl.$^2$ ..................... C07C 103/52; A61K 37/00
[52] U.S. Cl. .............................. 260/112.5 R; 424/177
[58] Field of Search .................. 260/112.5 R; 424/177

[56] References Cited

U.S. PATENT DOCUMENTS

| | | | |
|---|---|---|---|
| 3,862,111 | 1/1975 | Low et al. | 260/112.5 R |
| 3,886,134 | 5/1975 | Sipos et al. | 260/112.5 R |
| 3,975,365 | 8/1976 | Mazur | 260/112.5 R |
| 3,976,770 | 8/1976 | Bumpus et al. | 260/112.5 R |

*Primary Examiner*—Delbert R. Phillips
*Attorney, Agent, or Firm*—Karl F. Ross

[57] ABSTRACT

Angiotensin II analog of the formula I $$\text{X-Arg-Val-Tyr-Ile-His-Pro-Y} \qquad (I)$$

wherein
X is a radical derived from an aliphatic α-aminooxy-carboxylic acid and
Y is a radical derived from an aliphatic α-amino-carboxylic acid,
and acid addition salts and complexes thereof with antagonistic properties useful in the diagnosis and treatment of hypertensions depending on renin.

5 Claims, No Drawings

ANGIOTENSIN II ANTAGONIST PEPTIDES CONTAINING AN ALPHA-AMINOOXYACID IN THE POSITION-1

This invention relates to peptides of the formula I

X-Arg-Val-Tyr-Ile-His-Pro-Y    (I)

having antiotensin II antagonistic properties and to a process for the preparation of same.

In the general formula I
- X is a radical derived from an aliphatic α-aminooxy-carboxylic acid and
- Y is a radical derived from an aliphatic α-amino-carboxylic acid.

The preferred representatives of the radicals derived from an aliphatic α-aminooxy-carboxylic acid represented by X are aminooxyacetyl and α-aminooxy-propionyl groups, while Y preferably represents a leucyl, isoleucyl, alanyl or threonyl group.

Acid-addition salts and complexes of the peptides having the formula I are also within the scope of this invention.

Angiotensin II is an octapeptide having a hypertensive activity. In the organism, angiotensin I is prepared from α-globulin produced by the liver by means of an enzyme called renin, liberated by the kidney. In the organism this compound is converted to angiotensin II.

The first angiotensin II analog was reported in 1970. It was found that this compound acted as a specific competitive inhibitor of antiotensin II in in vivo and in vitro tests as well [G. R. Marshall et al.: Proc. Natl. Acad. Sci. USA 67, 1624 (1970); P. A. Khairralah et al.: J. Med. Chem. 13, 181 (1970)]. This observation brought about wide-spread interest and stimulated numerous laboratories to synthesize and observe new angiotensin II analogs, which possess antagonistic properties and thus may be used to diagnose or even treat hypertension depending on the liberation of renin. It turned out at the very beginning of this research that analogs in which the 8-Phe group was substituted by an amino acid having an aliphatic side-chain were the most promising compounds for this purpose. This change in the structure of the angiotensin II molecule means practically the disappearence of agonistic activity and the appearance of a strong antagonistic activity [D. Gagnon et al.: Br. J. Pharmacol., 43, 409 (1971), D. T. Pals et al.: Circ. Res., 29, 664 (1971)]. The antagonistic activity can considerably be increased when—in addition to the modification carried out in the 8-position—the 1-Asp group is replaced by a Sar unit [D. T. Pals et al.: Circ. Res., 29, 673 (1971)]. (Sar$^1$,Ala$^8$)-angiotensin II prepared in this way has already been put into circulation. The advantageous properties of this compound are attributed to a decrease in the in vivo enzymatic decomposition and to its great affinity to the receptor sites.

As to the use of the antagonistic analogs of angiotensin II one can find their application in the diagnosis and, in some instances, in the treatment of hypertensions depending on renin, see [D. Ganton and F. Gross: Med. Klin., 71, 2043 (1976); J. L. Marx: Science 194, 821 (1976); P. Needelman and G. R. Marschall: Fed. Proc. 35, 2486 (1976)].

A comparison of the structure and biological activity of angiotensin II analogs prepared until now has furnished some very important information for the interpretation of agonistic-antagonistic activity [M. C. Khosla et al.: "Handbook of Experimental Pharmacology" vol. 37, I. H. Page and P. M. Bumpus eds. 1974; G. R. Marshall: Fed. Proc. 35, 2494 (1976)].

At the center of present research work there is the preparation of new antagonists devoid of undesired side-effects and possessing a longer biological half-life [M. C. Khosla et al.: J. Med. Chem. 19, 244 (1976); ibid. 20, 253 (1977)].

It has now been found that by replacing the 8-phenylalanine moiety in the molecule of angiotensin II with an aliphatic α-amino-carboxylic acid radical and simultaneously attaching an aliphatic α-aminooxy-carboxylic acid radical to the 1-position it is possible to obtain new angiotensin II competitive inhibitors which considerably decrease hypertension induced by renin in in vivo tests even in case of subcutaneous administration.

According to the invention, compounds of the formula I

X-Arg-Val-Tyr-Ile-His-Pro-Y    (I)

wherein X and Y are as defined above, are prepared by reacting a reactive heptapeptide derivative of the formula II H-Arg(A)-Val-Tyr(B)-Ile-His(E)-Pro-Y-OG    (II)

wherein
- A is a group suitable for temporary protection of the guanidino group of Arg,
- B stands for a group suitable for temporary protection of the aromatic hydroxyl group of Tyr,
- E is a group suitable for temporary protection of the imidazolo group of His,
- G is hydrogen or a group suitable for the protection of the carboxyl group of the C-terminal aliphatic amino acid, which protecting group is stable under mild acid conditions but can be split off by treatment with strong acids or bases, and
- Y has the same meaning as defined above, with a reactive aminooxy-carboxylic acid derivative of the formula III

W-X-M    (III)

wherein
- X is as defined above,
- W is a protecting group removable by acidolysis, and
- M stands for a hydroxyl group or an activating group known per se, and splitting off the protecting groups from the compounds of the formula IV W-X-Arg(A)-Val-Tyr(B)-Ile-His(E)-Pro-Y-OG    (IV)

obtained, wherein
W, X, Y, A, B, E and G are as defined above, selectively, one after the other or simultaneously, in a single reaction step, and, if desired, converting a compound of the formula I obtained into an acid-addition salt or a complex thereof.

In the compounds of the formula II, A preferably represents a nitro or tosyl group, B preferably stands for a benzyl or substituted benzyl group; and E preferably is a dinitrophenyl group. In the starting compounds of the formula III, W preferably is benzyloxycarbonyl or tert.-butoxycarbonyl, X preferably is aminooxyacetyl or -aminooxypropionyl and M preferably is pivaloyloxy, nitrophenoxy, 2,3,5-trichlorophenoxy, pentachlorophenoxy, pentafluorophenoxy, N-succinimidoxy or azido.

The reactive heptapeptide derivatives of the formula II used as the starting material in the synthesis of a compound of this invention can be prepared by any method known in the chemistry of peptides. An appropriate method is described for example in the Hungarian Patent Specification No. 168,431. According to this method the functional groups of the side-chains are protected with groups which are stable under the conditions of acidolysis carried out when eliminating the protecting groups after coupling.

According to a preferred embodiment of the process according to the invention for the temporary protection of the carboxyl group of the C-terminal amino acid p-nitro-benzyl group (NB) is used; the hydroxyl group of tyrosin is protected by a benzyl group (Bzl); for the protection of the imidazole ring of histidine a dinitrophenyl group (Dnp) is used; while the guanidino group of arginin is protected by a tosyl group (Tos). All these protecting groups are stable under mild acid conditions, consequently the N-terminal t-butoxycarbonyl group (Boc) can be eliminated without any risk of splitting off these groups. The elimination of the dinitrophenyl group can be carried out by thiolysis and the remaining protecting groups can be split off by means of hydrogen fluoride.

Compounds of the formula I can be purified in a manner known per se, preferably by a carboxymethylcellulose ion-exchanger chromatography. As a result of this technology compounds are generally obtained as lyophilized powders which can easily be transformed into various salts or complexes.

The antagonistic activity of the compounds having the formula I was tested on narcoticized male cats. The blood pressure was measured on the cervical artery. The tests were performed by introducing a Hypertension (CIBA) infusion into a lateral femoral vane at a speed of 0.5 μg/kg/min. When the increase in blood pressure was stabilized, the aqueous, physiological or carrier-containing solutions of the test compounds and Saralasin were administered in a single dose, intravenously or subcutaneously, and the decrease in blood pressure was measured.

In the Table I the decrease in the arterial blood pressure under the influence of an intravenous administration of the test compounds is illustrated. For comparison Saralasin is used. The data set forth in the Table 1 were obtained by calculating the average of the results of 6 experiments. The margins of error indicate the scatter of the main value.

Table 1

The influence of various angiotensin II analog administered intravenously on the blood pressure, under i.v. infusion of angiotensin II

| Analogue | Decrease in blood pressure (mmHg) after administration of | |
|---|---|---|
| | 10 μg/kg   i.v. doses | 20 μg/kg |
| (Aminooxyacetyl$^1$, Leu$^8$)-AngII | −33±3.6 | −42±4.2 |
| (D-∞-Aminooxypropionyl$^1$ Leu$^8$)-AngII | −30±3.4 | −38±3.8 |
| (Aminooxyacetyl$^1$, Ile$^8$)-AngII | −28±2.0 | −40±5.7 |
| Saralasin | −41±2.5 | — |

From the data set forth in the above Table 1 it can be clearly seen that every angiotensin II analogue substituted with an aliphatic α-aminooxycarboxylic acid in the 1-position possesses a significant blood pressure; decreasing activity. The extent of the activity is proportional to the dose employed.

Tests were carried out also in case of subcutaneous administration. It should be noted that this route of administration for angiotensin II or analog thereof has not been published in the literature before. For subcutaneous administration a physiological saline solution containing the compound to be tested was supplemented with carboxymethylcellulose and gelatine, respectively. The results corresponding to the average of five separate tests are set forth in Table 2 below. The margins of error are related to the main value.

Table 2

The influence of various angiotensin II analog administered subcutaneously on the blood pressure under i.v. infusion of angiotensin II

| Analogues | Dose | Additive to the Solution | Decrease in the blood pressure (mmHg) after | | | |
|---|---|---|---|---|---|---|
| | | | 15 | 30 | 60 | 120 |
| | | | minutes | | | |
| (Aminooxyacetyl$^1$ Leu$^8$)-Ang-II | 200 | CMC | −21±5.8 | −26±7.2 | −13±9.4 | −5±7.8 |
| | 200 | gelatine | −23±2.0 | −21±2.2 | −10±2.8 | −1±51 |
| (D-∞-aminooxypropionyl$^1$Leu$^8$)-Ang-II | 200 | CMC | −21+6.7 | −24+5.7 | −16+5.1 | −1+4.0 |
| | 200 | gelatine | −24±5.7 | −21±5.6 | −9±5.7 | −3±8.8 |

According to the data given hereinabove the subcutaneously administered new compounds of this invention decrease the high blood pressure induced intentionally, in a significant manner, even 60 minutes after administration.

The peptides according to the invention as well as pharmaceutically acceptable salt and complexes thereof are used for pharmacological purposes in the form of conventional pharmaceutical compositions. The term "pharmaceutically acceptable complexes" of the peptides according to the invention is used herein to refer to complex compounds formed with certain, for instance organic materials, endowing the peptides with a retarded activity. Typical representatives of these compounds are gelatines, carboxymethylcelluloses, alginic acid esters, poly(fluoroethinephosphates), amino acid polymers or other polymers and copolymers. As pharmaceutically acceptable salts the conventional, pharmaceutically acceptable acid addition salts, e.g., acetates are used.

The pharmaceutical compositions contain the compounds according to the invention in admixture with organic or inorganic carriers suitable for enteral or parenteral administration. Thus pharmaceutical compositions may be formulated as solid lyophilizates, in which various inert compounds not reacting with peptides, e.g., hydrocarbons can be used as carriers. When the pharmaceutical compositions are formulated as dilute or concentrated suspensions or emulsions, they contain also various preserving agents and stabilizing agents.

Pharmaceutical compositions containing the compounds according to the invention may be used for differenciated detection of renal hypertensions as well as for the treatment of every syndrome caused by an increased renal blood pressure.

Further details of the invention are illustrated by the following non-limiting Examples. The abbreviations used in the Examples correspond to those generally used in the literature (J. Biol. Chem. 247, 977 (1972)). The α-aminooxy acids are designated by the syllable "O" put before the symbol corresponding to the amino acid in question. Thus for example OGly stands for aminooxyacetic acid; OAla represents α-aminooxypropionic acid etc. Further abbreviations are for instance: PFP=pentafluorophenyl and Z=carbomethoxy.

During the process according to the invention evaporation is always carried out in a Büchi Rotavapor equipment. The melting points were determined in a Dr. Tottoli apparatus (made by Büchi). Thin layer chromatography was carried out on "Kieselgel nach Stahl" silica gel plates (E. Merck, Darmstadt). The chromatograms were developed by the following solvent mixtures:

1. ethyl acetate: (20:6:11 mixture of pyridine/acetic acid/water)=95:5
2. ethyl acetate: (20:6:11 mixture of pyridine/acetic acid/water)=90 9 10
3. ethyl acetate: (20:6:11 mixture of pyridine/acetic acid/water)=80:20
4. ethyl acetate: (20:6:11 mixture of pyridine/acetic acid/water)=70:30
5. 4:1:5 mixture of n-butanol/acetic acid/water
6. 30:6:20:24 mixture of n-butanol/acetic acid/pyridine/water
7. 1:1:1:1 mixture of n-butanol/ethyl acetate/acetic acid/water.

In the Examples when indicating the $R_f$ values reference is made to the serial numbers of the above solvent systems.

Paper electrophoresis was accomplished in a LMIM medium-voltage horizontal equipment, on an MN 214 paper, in a PH=1.9 buffer solution, beside glutaminic acid. Voltage: 450 V, time: 3 hours.

The thin layer chromatograms were developed partly with a ninhydrine solution partly with a conventional chlorinating technique carried out with an o-tolidine-KJ solution.

The end-product was purified as described below:

The salts of the free peptides with hydrogen fluoride were purified on a "Sephacryl S-200 Sperfine" resin (Pharmacia, Fine Chemicals, Upsala, Sweden) by gradient eluting technique carried out with a 0.01 M (PH=4.5) and subsequently with a 0.4 M (PH=6.7) ammonium acetate solution. The eluates were registrated by an "LKB Uvicord II" apparatus (LKB, Upsala, Sweden) by means of an automatic fraction collector.

The main fraction was purified further as described below: 0.5 lit. of a carboxymethylcellulose (CMC-52) column were brought into equilibrium with the first buffer solution described above. 0.5 g. of a peptide were dissolved in 4 ml. of a 0.01 m ammonium acetate buffer. The solution obtained was overlayered on the carboxymethyl cellulose column. 1.5 lit. of a 0.01 M ammonium acetate solution were admixed with 1.5 lit. of a 0.4 M ammonium acetate solution in a gradient stirrer and gradient elution was carried out. The flow velocity was adjusted to 25 ml./hour and 10-ml. fractions were collected. The eluate leaving the column was continuously registrated by means of an LKB Uvicord-II apparatus. The purified end product was obtained by lyophilizing the main fraction.

EXAMPLE 1

(Aminooxyacetyl$^1$,Ile$^8$)-angiotensin II

Step 1

Boc-Arg(Tos)-Val-Tyr(Bzl)-Ile-His(Dnp)-Pro-Ile-ONB 4.5 g. (15 moles) of Ile-ONB are dissolved in 50 ml. of chloroform and to the solution 2.1 ml. of triethylamine and 3.81 g. (10 mmoles) of Boc-Pro-OPFP are added. The reaction mixture is stirred at room temperature for 20 minutes and thereafter shaken with water and a 10% aqueous citric acid solution. After drying and evaporation a protected peptide is obtained ($R_f^1$=0.8) which is immediately dissolved in 20 ml. of a 8 M solution of hydrochloric acid in dioxane. The solution is allowed to stand for 10 minutes and is diluted with dry ether and evaporated. The free dipeptide hydrochloride obtained ($R_f^3$=0.44) is dissolved in 30 ml. of chloroform, the pH-value is adjusted to 8 with triethyl amine and 8.8 g. (15 mmoles) of Boc-His(Dnp)-OPFP are added. After one and a half hours 1.65 ml. of N,N-dimethylaminoethylamine are added to the solution and after 15 minutes the reaction mixture is shaken with a 10% aqueous citric acid solution, 1 N aqueous hydrochloric acid solution, with water and finally with a 5% aqueous sodium bi-carbonate solution. After drying and evaporation the protected tripeptide ($R_f^1$=0.50) obtained is dissolved—without isolation—in 20 ml. of a 8 M solution of hydrochloric acid in dioxane and the free tripeptide ($R_f^4$=0.25) is precipitated upon addition of dry ether. The precipitate obtained is filtered off and washed with ether. Thereafter it is immediately dissolved in a mixture of 50 ml. of chloroform and 20 ml. of dimethyl formamide, the pH is adjusted to 8 with triethyl amine and 6.0 g. (15 mmoles) of Boc-Ile-OPFP are added to the solution. After 30 minutes the solvent is replaced by ethyl acetate and the mixture is shaken with a 100% aqueous solution of citric acid and with a 1 M aqueous hydrochloric acid solution and finally with water. Drying and subsequent evaporation of the organic solution affords a protected tetrapeptide ($R_f^2$=0.65) which is then isolated by means of a 1:9 mixture of ether and n-hexane. It is then dissolved in 25 ml. of a 8 M solution of hydrochloric acid in dioxane and the free tetrapeptide ($R_f^4$=0.41) is precipitated after 30 minutes, by means of dry ether. The precipitate is filtered off and washed with ether. It is immediately dissolved in a 1:1 mixture of dimethyl formamide and chloroform (70 ml.), the pH of the solution is adjusted to 8 with triethyl amine and 6.0 g. (11.5 mmoles) of Boc-Tyr(Bzl)-OPFP are added. The solution is allowed to stand for 15 minutes, whereupon the solvent is replaced by ethyl acetate. 0.66 ml. of N,N-dimethylaminoethylamine are added and after 15 minutes the mixture is shaken with a 10% aqueous solution of citric acid, with a 1 M aqueous hydrochloric acid and finally with water. Drying and evaporation of the product obtained affords a protected pentapeptide ($R_f^2=0.59$) which is precipitated with ether, filtered off and washed with ether. It is then dissolved in 20 ml. of a 8 M solution of hydrochloric acid in dioxane and allowed to stand for 15 minutes. The free pentapeptide ($R_f^4=0.4$) is then precipitated with dry ether, filtered off and washed with ether. It is immediately dissolved in 50 ml. of dimethyl formamide, the pH-value of the solution is adjusted to 8 with triethyl amine and 4.62 g. (12 mmoles) of Boc-Val-OPFP are added. After one hour the solvent is replaced by chloroform and the solution is shaken with a 10% aqueous solution of citric acid, 1 M aqueous hydrochloric acid solution and finally with water. Drying and evaporation of the mixture affords a protected hexapeptide ($R_f^2=0.56$), which is then isolated by means of ether and washed with ether. The product is dissolved in 20 ml. of a 8 M solution of hydrochloric acid in dioxane and free hexapeptide ($R_f^4=0.47$) is precipitated with dry ether. The precipitate is filtered off and washed with ether. It is immediately dissolved in 50 ml. of dimethyl formamide and the pH-value of the solution is adjusted to 8 with triethyl amine. 7.2 g. (12 mmoles) of Boc-Arg(Tos)-OPFP are added, the mixture is stirred for one hour and the solvent is replaced by chloroform. The solution obtained is shaken with a 10% aqueous citric acid solution, 1 N aqueous hydrochloric acid solution and finally with water. Upon drying and evaporation the residue is triturated with ether to give 12.4 g. of the corresponding protected heptapeptide (80% of theoretical). Melting point: 189° to 192° C.; $R_f^2=0.55$.

Step 2

Boc-OGly-Arg(Tos)-Val-Tyr-Ile-His-Pro-Ile-Oh 3.1 g. (2 mmoles) of Boc-Arg(Tos)-Val-Tyr(Bzl)-Ile-His(Dnp)-Pro-Ile-ONB are dissolved in 5 ml. of dimethylformamide and 2.9 ml. of 2-mercaptoethanol are added. After one hour the peptide is precipitated with dry ether, filtered, washed with ether and purified by dissolution in methanol and precipatation with ether. 2.0 g. (74%) of Boc-Arg(Tos)-Val-Tyr(Bzl)-Ile-His-Pro-Ile-ONB are obtained ($R_f^2=0.1$). The product is dissolved in 30 ml. of a 5:1:1 mixture of methanol, acetic acid and water and 1.0 g. of a 10% palladium on charcoal catalyst are added. Thereafter hydrogen is bubbled through the solution for 5 hours, the catalyst is filtered off, whereupon the solution is evaporated and triturated with ether. 1.22 g. (75%) of a partly protected heptapeptide of the formula Boc-Arg(Tos)-Val-Tyr-Ile-His-Pro-Ile-OH are obtained. $R_f^5=0.8$. 0.6 g. (0.5 mmoles) of the product obtained are dissolved in 5 ml. of a 8 M solution of hydrochloric acid in dioxane and after 20 minutes of stirring the free heptapeptide ($R_f^4=0.1$) is filtered off and washed with ether. It is immediately dissolved in 15 ml. of dimethyl formamide, the pH-value is adjusted to 8 with triethylamine and 0.45 g. (1.2 mmoles) of Boc-OGly-OPFP are added. After 30 minutes the reaction mixture is evaporated, the residue is dissolved in 30 ml. of a 3:1 mixture of chloroform and dimethyl formamide, and the solution is shaken with a 10% aqueous citric acid solution and subsequently with water. The extract is dried and evaporated and the residue is triturated with ethyl acetate. After filtration and washing with ether 0.46 g. (72%) of Boc-OGly-Arg(Tos)-Val-Tyr-Ile-His-Pro-Ile-OH are obtained. $R_f^3=0.23$; $R_f^4=0.40$.

Step 3

Elimination of the protecting groups 0.46 g. (0.35 mmoles) of Boc-OGly-Arg(Ios)-Val-Tyr-Ile-OH are dissolved in 2 ml. of liquid hydrogen fluoride and 0.5 ml. of thioanisol are added. The solution is kept at 0° C. for one hour, and the peptide is precipitated by ether, filtered off and washed with ether. 0.35 g. (100%) of the product are obtained. The hydrogen fluoride salt obtained is purified as described hereinbefore. The characteristics of the (aminooxyacetyl$^1$,Ile$^8$)-angiotensin II analog are as follows:

$R_f^5=0.26$; $R_f^6=0.56$; $R_f^7=0.57$; $E_{Glu}=1.00$.

Amino acid analysis: Pro: 1.02/1/; Val: 1.0/1/; Ile: 1.98/2/;

Tyr: 0.65/1/; His: 1.0/1/; Arg: 1.03/1/.

EXAMPLE 2

(L-α-Aminooxypropionyl$^1$,Ile$^8$)-angiotensin II

Step 1

Boc-OAla-Arg(Tos)-Val-Tyr-Ile-His-Pro-Ile-OH 0.6 g. (0.5 mmoles) of Boc-Arg(Tos)-Val-Tyr-Ile-His-Pro-Ile-OH (prepared in Step 2 of Example 1) are dissolved in 5 ml. of a 8 M solution of hydrochloric acid in dioxane. The solution is allowed to stand for 20 minutes whereupon the free heptapeptide ($R_f^4=0.1$) is precipitated with dry ether, filtered and washed with ether. It is immediately dissolved in 20 ml. of dimethyl formamide, the pH-value is adjusted to 8 with triethyl amine and 0.7 g. (1.9 mmoles) of Boc-OAla-OPFP are added. After 30 minutes the solution is evaporated and the residue is dissolved in 30 ml. of a 3:1 mixture of chloroform and dimethyl formamide. The solution is shaken with a 10% aqueous citric acid solution and subsequently with water. After drying and evaporation the residue is triturated with ethyl acetate, filtered and washed to give 0.55 g. (84%) of the title compound. $R_f^4=0.43$; $R_f^5=0.80$.

Step 2

Elimination of the protecting groups 0.52 g. (0.42 mmoles) of Boc-OAla-Arg(Tos)-Val-Tyr-Ile-His-Pro-Ile-OH are dissolved in 2 ml. of liquid hydrogen fluoride and 0.55 ml. of thioanisol are added. The solution is kept at 0° C. for one hour, precipitated with dry ether, filtered and washed with ether. 0.41 g. of (OAla$^1$, Ile$^8$)-angiotensin II are obtained. After purifying the product as described above a product having the following characteristics is obtained: $R_f^5=0.32$; $R_f^6=0.58$; $R_f^7=0.59$; $E_{Glu}=1.0$.

Amino acid analysis: Pro: 1.0/1/; Val: 1.1/1/; Ile: 2.02/2/;

His: 0.9/1/; Tyr: 0.95/1/; Arg: 1.05/1/.

EXAMPLE 3

(Aminooxyacetyl¹,Leu⁸)-angiotensin II

Step 1

Boc-Arg(Tos)-Val-Tyr(Bzl)-Ile-His(Dnp)-Pro-Leu-ONB 4.2 g. (12 mmoles) of Leu-ONB.HBr are dissolved in 50 ml. of chloroform and 1.68 ml. of triethyl amine and 3.81 g. (10 mmoles) of Boc-Pro-OPFP are added. The solution is stirred at room temperature for 20 minutes, whereupon it is shaken with a 10% aqueous citric acid solution and subsequently with water. The protected dipeptide ($R_f^1 = 0.8$) obtained after drying and evaporation is dissolved in 20 ml. of a 8 M solution of hydrochloric acid in dioxane and after 10 minutes the solution is diluted with dry ether and evaporated. The free dipeptide ($R_f^4 = 0.56$) is dissolved in 50 ml. of chloroform without isolation, the pH-value of the solution is adjusted to 8 with triethylamine and 8.8 g. (15 mmoles) of Boc-His(Dnp)-OPFP are added. After 30 minutes 1.65 ml. of N,N-dimethylaminoethylamine are added to the solution which is allowed to stand for 10 minutes. Thereafter it is shaken with a 10% aqueous citric acid solution, 1 N aqueous hydrochloric acid solution, sodium bi-carbonate solution and finally with water. The extract is dried and evaporated and the protected tripeptide ($R_f^1 = 0.65$) obtained is dissolved in 25 ml. of a 8 M solution of hydrochloric acid in dioxane, without isolation. The free tripeptide is precipitated with dry ether ($R_f^4 = 0.47$), filtered off and washed. It is immediately dissolved in a mixture of 50 ml. of chloroform and 20 ml. of dimethyl formamide, the pH is adjusted to 8 with triethylamine and 6.0 g. (15 mmoles) of Boc-Ile-OPFP are added. After 30 minutes the solvent is replaced by ethyl acetate and the solution is shaken with a 10% aqueous citric acid solution and subsequently with water. Upon drying and evaporation the protected tetrapeptide ($R_f^1 = 0.65$) is isolated by means of a 7:3 mixture of n-hexane and ether. It is then dissolved in 25 ml. of a 8 M solution of hydrochloric acid in dioxane and after 15 minutes the free tetrapeptide ($R_f^4 = 0.65$) is precipitated with dry ether, filtered and washed with ether. It is then precipitated with dry ether, filtered and washed with ether. It is immediately dissolved in 50 ml. of a 1:1 mixture of chloroform and dimethyl formamide, the pH-value is adjusted to 8 with triethylamine and 6.0 g. (11.5 mmoles) of Boc-Tyr-OPFP are added. After 15 minutes the solvent is replaced by ethyl acetate, 0.66 ml. of N,N-dimethylaminoethylamine are added and the solution is allowed to stand for 15 minutes. It is then shaken with a 10% aqueous citric acid solution, 1 N aqueous hydrochloric acid solution and finally with water. Upon drying and evaporation the protected pentapeptide ($R_f^2 = 0.8$) is isolated with ether. The product obtained ($R_f^4 = 0.8$) is dissolved in 20 ml. of a 8 M solution of hydrochloric acid in dioxane, precipitated upon addition of dry ether, filtered and washed with ether. It is immediately dissolved in 50 ml. of dimethyl formamide, the pH is adjusted to 8 with triethylamine and 3.85 g. (10 mmoles) of Boc-Val-OPFP are added. After one hour the solvent is replaced by chloroform, shaken in a conventional manner and the protected hexapeptide ($R_f^2 = 0.82$) is isolated by means of ether. It is then dissolved in 20 ml. of a 8 M solution of hydrochloric acid in dioxane and after 15 minutes the free hexapeptide ($R_f^3 = 0.55$) is isolated by means of dry ether. It is immediately dissolved in 40 ml. of dimethyl formamide, the pH is adjusted to 8 with triethylamine and 6.0 g. (10 mmoles) of Boc-Arg(Tos)-OPFP are added. After 30 minutes the solvent is replaced by chloroform and the solution is shaken with a 1 N aqueous hydrochloric acid solution and subsequently with water. The extract is dried and evaporated to give a protected heptapeptide ($R_f^2 = 0.62$), which is isolated by means of ethanol. Yield: 7.5 g. (50% related to the starting Boc-Pro-OPFP). Melting point: 186° to 190° C.

Step 2

Boc-OGly-Arg(Tos)-Val-Tyr-(Bzl)-Ile-His-Pro-Leu-OH 3.45 g. (2.26 mmoles) of Boc-Arg(Tos)-Ile-His(Dnp)-Pro-Leu-ONB are dissolved in 10 ml. of dimethyl formamide, 6.6 ml. of 2-mercaptoethanol are added and the partly protected heptapeptide is precipitated with dry ether after two hours of standing. The product is purified by methanol/ether precipitation. 2.9 g. (93%) of Boc-Arg(Tos)-Val-Tyr(Bzl)-Ile-His-Pro-Leu-ONB are obtained. $R_f^2 = 0.12$; $R_f^3 = 0.26$. The product is dissolved in 40 ml. of a 5:1:1 mixture of methanol, acetic acid and water, 1.0 g. of a 10% palladium on charcoal catalyst are given and hydrogen is bubbled through the mixture for 6 hours. The catalyst is filtered off and the solution is evaporated. The residue is triturated with ether to give 2.5 g. (89%) of the product. $R_f^5 = 0.75$; $R_f^4 = 0.20$. 1.1 g. (1 mmole) of Boc-Arg(Tos)-Val-Tyr-Ile-His-Pro-Leu-OH are dissolved in 10 ml. of a 8 M solution of hydrochloric acid in dioxane. After 30 minutes the free heptapeptide ($R_f^4 = 0.08$) is precipitated with dry ether, filtered off and washed with ether. It is immediately dissolved in 10 ml. of dimethyl formamide, the pH of the solution is adjusted to 8 with triethylamine and 0.54 g. (1.5 mmoles) of Boc-OGly-OPFP are added. After 30 minutes the solution is diluted with 30 ml. of chloroform and shaken with water. The extract is dried and evaporated and the residue is triturated with ethyl acetate, filtered and washed with ethyl acetate. 1.05 g. (86%) of Boc-OGly-Arg(Tos)-Val-Tyr-Ile-His-Pro-Leu-OH are obtained. $R_f^3 = 0.23$; $R_f^4 = 0.40$.

Step 3

Elimination of the protecting groups 0.9 g. (0.73 mmoles) of Boc-OGly-Arg(Tos)-Val-Tyr-Ile-His-Pro-Leu-OH are dissolved in 5 ml. of liquid hydrogen fluoride and 1.5 ml. of thioanisol are added. The reaction mixture is kept at 0° C. for 1.5 hours, whereupon it is treated with dry ether and the peptide precipitated is washed with ether and filtered off. 0.55 g. (80%) of (OGly¹,Leu⁸)-angiotensin II are obtained, which is purified in a manner described earlier. $R_f^5 = 0.33$; $R_f^6 = 0.60$; $R_f^7 = 0.55$; $E_{Glu} = 1.18$.

Amino acid analysis: Pro: 1.0/1/; Val: 1.0/1/; Ile 1.0/1/;
Leu: 1.1/1/; His: 0.95/1/; Arg: 1.0/1/; Tyr: 0.7/1/.

EXAMPLE 4

(D-α-Aminooxypropionyl¹,Leu⁸)-angiotensin II

Step 1

Boc-D-OAla-Arg(Tos)-Val-Tyr-Ile-His-Pro-Leu-OH 1.1 g. (1 mmole) of Boc-Arg(Tos)-Val-Tyr-Ile-His-Pro-Leu-OH are dissolved in 10 ml. of a 8 M solution of hydrochloric acid in dioxane. After 30 minutes the free heptapeptide is precipitated with dry ether, filtered and washed with ether. It is immediately dissolved in 10 ml. of dimethyl formamide, the pH is adjusted to 8 with triethylamine and 0.56 g. (1.5 mmoles) of Boc-D-OAla-OPFP are added to the solution. After 30 minutes the solution is diluted with chloroform and shaken with water. After drying and evaporation the residue is triturated with ethyl acetate, filtered and washed with ethyl acetate. Thus 0.95 g. (77%) of Boc-D-OArg(Tos)-Val-Tyr-Ile-His-Pro-Leu-OH are obtained. $R_f^4 = 0.29$.

Step 2

Elimination of the protecting groups 0.95 g. (0.77 mmoles) of Boc-D-OAla-Arg(Tos)-Val-Tyr-Ile-His-Pro-Leu-OH are dissolved in 4 ml. of liquid hydrogen fluoride and 1.2 ml. of thioanisol are added. The solution is kept at 0° C., the substance is precipitated with dry ether, filtered and washed with ether. In this way 0.6 g. (90%) of (D-OAla$^1$,Leu$^8$)-angiotensin II are obtained, which can be purified in a conventional manner. $R_f^5 = 0.33$; $R_f^6 = 0.61$; $R_f^7 = 0.56$; $E_{Glu} = 1.10$.

Amino acid analysis: Pro: 1.02/1/; Val: 1.0/1/; Leu: 1.02/1/; Ile: 1.03/1/; His: 1.01/1/; Arg: 0.92/1/; Tyr: 0.8/1/.

What we claim is:
1. A peptide of the formula:

X-Arg-Val-Tyr-Ile-His-Pro-Y wherein
X is aminooxyacetyl or alpha-aminooxypropionyl and Y is leucyl, isoleucyl, alanyl or threonyl or an acid addition salt or complex thereof.
2. A peptide as claimed in claim 1, which is OGly-Arg-Val-Tyr-Ile-His-Pro-Leu-OH or an acid-addition salt or complex thereof.
3. A peptide as claimed in claim 1, which is OAla-Arg-Val-Tyr-Ile-His-Pro-Leu-OH or an acid addition salt or complex thereof.
4. A peptide as claimed in claim 1 which is OGly-Arg-Val-Tyr-Ile-His-Pro-Ile-OH or an acid-addition salt or complex thereof.
5. A peptide as claimed in claim 1, which is OAla-Arg-Val-Tyr-Ile-His-Pro-Ile-OH or an acid-addition salt or complex thereof.

* * * * *